United States Patent
Eden et al.

(10) Patent No.: US 12,224,150 B2
(45) Date of Patent: Feb. 11, 2025

(54) SYSTEMS AND METHODS FOR IMPROVING X-RAY SOURCES WITH SWITCHABLE ELECTRON EMITTERS

(71) Applicant: NANO-X IMAGING LTD., Neve Ilan (IL)

(72) Inventors: Nir Eden, Kfar Saba (IL); Amir Ben Shalom, Modiin (IL); Hitoshi Masuya, Kashiwa (JP)

(*) Notice: Subject to any disclaimer, the term of this patent is extended or adjusted under 35 U.S.C. 154(b) by 111 days.

(21) Appl. No.: 17/766,245

(22) PCT Filed: Oct. 4, 2020

(86) PCT No.: PCT/IB2020/059306
§ 371 (c)(1),
(2) Date: Apr. 3, 2022

(87) PCT Pub. No.: WO2021/064704
PCT Pub. Date: Apr. 8, 2021

(65) Prior Publication Data
US 2024/0047167 A1    Feb. 8, 2024

Related U.S. Application Data

(60) Provisional application No. 62/909,797, filed on Oct. 3, 2019, provisional application No. 62/909,794, filed on Oct. 3, 2019, provisional application No. 62/909,789, filed on Oct. 3, 2019.

(51) Int. Cl.
| | | |
|---|---|---|
| H01J 35/00 | (2006.01) | |
| A61B 6/00 | (2006.01) | |
| A61B 6/03 | (2006.01) | |
| A61B 6/40 | (2024.01) | |
| H01J 35/02 | (2006.01) | |
| H01J 35/06 | (2006.01) | |

(52) U.S. Cl.
CPC ............ *H01J 35/025* (2013.01); *A61B 6/032* (2013.01); *A61B 6/4007* (2013.01); *A61B 6/4488* (2013.01); *H01J 35/065* (2013.01)

(58) Field of Classification Search
CPC ................................ H01J 35/065; H01J 35/13
See application file for complete search history.

(56) References Cited

U.S. PATENT DOCUMENTS

| | | |
|---|---|---|
| 4,453,263 A | 6/1984 | Resnick et al. |
| 5,365,565 A | 11/1994 | Barbaric |
| 6,553,096 B1 | 4/2003 | Zhou et al. |
| 8,666,024 B2 | 3/2014 | Okunuki et al. |

(Continued)

FOREIGN PATENT DOCUMENTS

| | | |
|---|---|---|
| CN | 102543635 A | 7/2012 |
| RU | 2191997 C2 | 10/2022 |
| WO | 2018086744 A2 | 5/2018 |

*Primary Examiner* — Dani Fox
(74) *Attorney, Agent, or Firm* — AlphaPatent Associates Ltd.; Daniel J. Swirsky

(57) ABSTRACT

Systems and methods for improving x-ray sources with switchable electron emitters. Improved systems may use the functionality of the switchable electron emitters in various configurations to provide power regulation, multidimensional analysis, and electron beam forming so as to increase the durability and the reliability of the system. Cooling mechanisms may be used to further protect the anode from deterioration over time.

11 Claims, 18 Drawing Sheets

(56) References Cited

U.S. PATENT DOCUMENTS

| | | | |
|---|---|---|---|
| 8,699,657 B2 | 4/2014 | Baeumer | |
| 9,490,099 B2 | 11/2016 | Mackie et al. | |
| 10,159,455 B2 | 12/2018 | Takanaka et al. | |
| 2002/0094064 A1 | 7/2002 | Zhou et al. | |
| 2004/0076260 A1* | 4/2004 | Charles, Jr. | H01J 35/18 378/124 |
| 2005/0236573 A1 | 10/2005 | Vogtmeier | |
| 2005/0265520 A1 | 12/2005 | Huber et al. | |
| 2009/0041198 A1* | 2/2009 | Price | H01J 35/24 378/147 |
| 2009/0052615 A1 | 2/2009 | Ribbing et al. | |
| 2009/0185660 A1 | 7/2009 | Zou et al. | |
| 2013/0170608 A1 | 7/2013 | Weedon | |
| 2017/0150936 A1 | 6/2017 | Yoda | |
| 2017/0309436 A1* | 10/2017 | Peterson | H01J 37/15 |
| 2018/0068823 A1 | 3/2018 | Utschig et al. | |
| 2018/0184990 A1 | 7/2018 | Shin et al. | |
| 2018/0249566 A1 | 8/2018 | Proksa et al. | |

\* cited by examiner

SYSTEMS AND METHODS FOR IMPROVING X-RAY SOURCES WITH SWITCHABLE ELECTRON EMITTERS

CROSS-REFERENCE TO RELATED APPLICATIONS

This application is a U.S. National Phase Application under 35 U.S.C. 371 of International Application No. PCT/IB2020/059306, which has an international filing date of Oct. 4, 2020, and which claims the benefit of priority from U.S. Provisional Patent Application No. 62/909,789, filed Oct. 3, 2019, U.S. Provisional Patent Application No. 62/909,794, filed Oct. 3, 2019, and U.S. Provisional Patent Application No. 62/909,797, filed Oct. 3, 2019, the contents of which are incorporated by reference in their entirety.

FIELD OF THE DISCLOSURE

The disclosure herein relates to systems and methods for improving digitally switchable x-ray sources. In particular, the disclosure relates to coordinating the switching of a low voltage driver to control emission of electron beams towards an anode target of an x-ray source.

BACKGROUND

X-ray sources generally produce x-rays by accelerating a stream of electrons using a high voltage electric field towards an anode target. Typically the electron emitters of x-ray sources are hot filament cathodes. Such x-ray sources are difficult to control as the accelerating field requires high voltage and high voltage supplies are not readily switchable. Furthermore, hot filament cathodes have slow response times.

As a result typical x-ray sources may produce a steady stream of x-rays but because of the their long response times, they cannot produce x-ray pulses.

Thus, there is a need for controllable x-ray sources with fast response times. The invention described herein addresses the above-described needs.

SUMMARY OF THE EMBODIMENTS

According to one aspect of the presently disclosed subject matter, a retrofittable x-ray emission system is introduced which is configured to be retrofit to a computed tomography (CT) scanner. The retrofittable x-ray emission system may include an array of secondary x-ray sources directed towards the central axis of the CT scanner and are operable to be individually controlled.

Each of the secondary x-ray sources may include: at least one field emission type electron emitting construct; an anode target; at least one low voltage driving circuit for activating the at least one electron emitting construct; a high voltage supply for establishing an electron accelerating potential between the at least one electron emitting construct and the anode target; and at least one digital switching unit operable to selectively connect and disconnect the at least one low voltage driving circuit.

Where appropriate, at least one electron beam directing mechanism may be operable to direct a stream of electrons emitted by the electron emitting construct towards a desired point upon the anode target. Additionally, or alternatively, at least one electron beam shaping mechanism, such as a ring cathode or the like, may be provided for reducing the diameter of an electron beam emitted by the electron emitting construct.

A synchronizer may be operable to coordinate the timings between the at least one digital switching device, the at least one electron beam directing mechanism and the at least one electron beam shaping mechanism.

Optionally the secondary x-ray sources may further include at least one regulator in communication with a synchronizer and operable to send a monitor signal thereto indicating if the low voltage signal should be activated.

In some examples an anode cooling mechanism is provided to cool the anode. For example, the cooling mechanism may include at least one thermally conducting cooling pipe through which coolant passes from an inlet to an outlet.

It is another aspect of the disclosure to introduce an x-ray emission system comprising a field emission type electron emitting construct; an anode target; a low voltage driving circuit for activating the electron emitting construct; and a high voltage supply for establishing an electron accelerating potential between the electron emitting construct and the anode; a digital switching unit operable to selectively connect and disconnect the low voltage driving circuit; a synchronizer; and at least one regulator in communication with the synchronizer and operable to send a monitor signal thereto indicating if the low voltage signal should be activated.

Where Required the regulator may include a high voltage supply monitor configured and operable to monitor potential difference between the anode target and the electron emitter; a memory unit storing at least one reference value; and a comparator configured and operable to compare the potential difference between the anode target and the electron emitter with the at least one reference value. Accordingly, the memory unit may store an Upper High Voltage Threshold value HVupper and a Lower High Voltage Threshold value HVlower.

Accordingly, a method is taught for regulating the high voltage supply of an x-ray source by selectively triggering a low voltage signal to an electron emitting cathode. This method may include providing a regulator including a high voltage monitor, a comparator and a memory unit; storing an Upper High Voltage threshold value HVupper in the memory unit; storing a Lower High Voltage threshold value HVlower in the memory unit; the high voltage monitor monitoring the high voltage supplied between the electron emitting cathode and an anode target; the comparator deactivating the low voltage supply to the electron emitting cathode if the high voltage supply is above the Upper High Voltage threshold value HVupper; and the comparator activating the low voltage supply to the electron emitting cathode if the high voltage supply is below the Lower High Voltage threshold value HVupper.

Additionally or alternatively, the at least one regulator comprises a memory unit storing a High Voltage Supply Function HV(t), a time monitoring device; and a processor configured and operable to trigger a monitor signal when the High Voltage Supply Function HV(t) returns a value outside a required range. Accordingly another method is taught for regulating a high voltage supply of an x-ray source by selectively triggering a low voltage signal to an electron emitting cathode. This method may include providing a regulator including a time monitoring device, a regulator and a memory unit; storing an Upper High Voltage threshold value HVupper in the memory unit; storing a Lower High Voltage threshold value HVlower in the memory unit; storing a High Voltage Supply function HV(t) in the memory unit; the time monitoring device recording time elapsed; the processor calculating the value of HV(t) for current time elapsed; the processor deactivating the low voltage supply to the electron emitting cathode if a calculated value of HV(t) is above the Upper High Voltage threshold value HVupper; and the processor activating the low voltage supply to the electron emitting cathode if a calculated value of HV(t) is below the Lower High Voltage threshold value HVupper.

It is another aspect of the disclosure to introduce an x-ray emission system, comprising an electron anode target; an array of cold cathode electron sources configured to emit electrons towards the electron anode target; and a switching system for switching between the cold cathodes of the array; wherein the x-ray emitter device further comprises: at least one electron beam directing mechanism operable to direct a stream of electrons emitted by the at least one cold cathode electron source towards a desired point upon the electron anode target; and at least one electron beam shaping mechanism for reducing the diameter of an electron beam emitted by the at least one cold cathode electron source. Optionally, the electron beam shaping mechanism comprises a ring cathode configured such that an electron beam emitted by the cold cathode passes therethrough before striking the anode target.

Where required the directing mechanism comprises a variable DC power supply operable to maintain a required potential difference between a pair of electrodes thereby generating an electric field and deflecting electron beams emitted by the cold cathodes. Optionally, the at least one switching device comprises a multiplexer operable to switch sequentially between the cold cathode electron sources.

Accordingly it is another aspect of the disclosure to teach a method for generating a narrow beam of x-rays from an anode target. This method may comprise steps including: providing x-ray emitter device, comprising an array of cold cathode electron sources configured to emit electrons towards an electron anode target; providing a switching system for switching between the cold cathodes of the array; providing at least one electron beam directing mechanism; the switching system activating a first cold cathode to emit a stream of electrons; the electron beam directing mechanism directing the stream of electrons towards a first desired point upon the anode target; the switching system deactivating the first cold cathode to emit a stream of electrons; the switching system activating a next cold cathode to emit a next stream of electrons; the electron beam directing mechanism directing the stream of electrons towards a next desired point upon the anode target; the switching system deactivating the next cold cathode to emit a stream of electrons; repeating the steps of activating, directing and deactivating for each cold cathode; such that each cold cathode produces an electron beam incident upon different points of the anode target. Optionally the method further includes: providing at least one electron beam shaping mechanism; and reducing the cross section of each electron beam directed towards the anode target.

It is still another aspect of the disclosure to introduce a system for providing multidimensional x-ray imaging comprising: a primary x-ray source directed towards a central axis and configured to rotate around a central axis; and an x-ray detection unit configured to rotate around the central axis and to detect x-rays in the region diametrically opposed to the primary x-ray source and across the central axis therefrom; wherein the system further comprises an array of secondary x-ray sources arranged around the central axis and operable to be individually controlled.

Optionally, the array of secondary x-ray sources is arranged equidistantly around the central axis. Alternatively, the array of secondary x-ray sources may be arranged in an arc of a perimeter of a circle around the central axis. Where required the array of secondary x-ray sources are selected such that they have characteristic energy levels. Optionally the array of secondary x-ray sources have energy levels different from the primary x-ray source. Additionally, or alternatively, each secondary x-ray source of the array may have an associated x-ray shield configured to prevent x-rays emitted by the primary source from reaching the x-ray detection unit.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the various selected embodiments may be put into practice. In the accompanying drawings.

DETAILED DESCRIPTION

Figure 1:
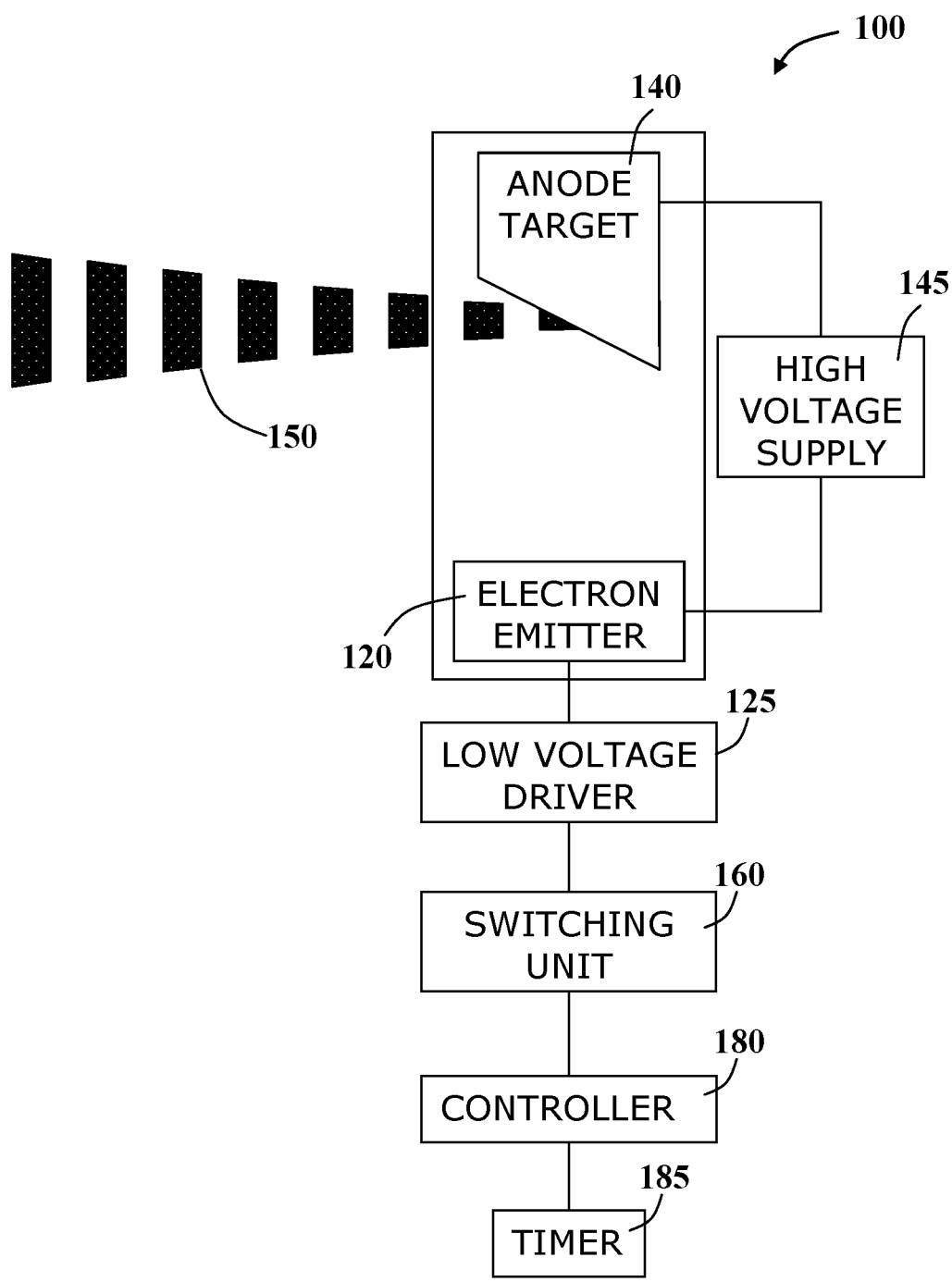
FIG. 1 is a block diagram representing selected elements of an embodiment of a switchable X-ray source.

Aspects of the present disclosure relate to system and methods for improving x-ray sources with switchable electron emitters. Improved systems may use the functionality of the switchable electron emitters in various configurations to provide power regulation, multidimensional analysis, and electron beam forming so as to increase the durability and the reliability of the system. Cooling mechanisms may be used to further protect the anode from deterioration over time.

In various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally, or alternatively, the data processor may access a non-volatile storage, for example, a magnetic hard-disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting.

FIG. 1 is a block diagram representing selected elements of an embodiment of a switchable x-ray source 100. The digitally switchable x-ray emission system 100 includes an electron emitter 120, an anode target 140, a high voltage supply 145, a low voltage driver 125, a switching unit 160 a controller 180 and a timer 185

The electron emitter 120 may be a cold cathode such as a low voltage activated field emission type electron emitting construct configured and operable to release electrons when stimulated by a low voltage. Accordingly, the low voltage driver 125 may include a low voltage driving circuit for activating the electron emitting construct;

The anode target 140 may comprise a metallic target selected such that x-rays 150 are generated when it is bombarded by accelerated electrons from the electron emitter 120. The anode 140 may be constructed of molybdenum, rhodium, tungsten, or the like or combinations thereof.

The high voltage supply 145 wired between said electron emitting construct 120 and the anode 140 is provided for establishing an electron accelerating potential between said electron emitting construct 120 and the anode 140.

It is a particular feature of the digitally switchable x-ray emission system 100 that the digital switching unit 160 is provided to selectively connect and disconnect the low voltage driving circuit 125 thereby selectively activating and deactivating the electron emitting construct 120. Accordingly, emission of the electrons may be controlled by the digital switching system 160.

When the emitting construct 120 is activated electrons are accelerated towards said anode target 140 and a pulse of x-rays 150 is generated. As a result, x-ray emission from the anode 140 may be controlled digitally by the switching unit 160.

The controller 180 may be provided to generate an activation signal which can control the switching rate of the digital switching unit 160. It is particularly noted that in contrast to high voltage switching systems, because the activation signal is a low voltage signal, the response time of the electron emitter is much shorter than the response time of switching the high voltage accelerating potential.

As a result of the reduced response time of the low voltage switching unit, a timer 185 may be provided to generate a fixed clock signal and a high frequency activation signal may be provided consisting of a series of short duration gate pulses at regular intervals.

Figure 2:
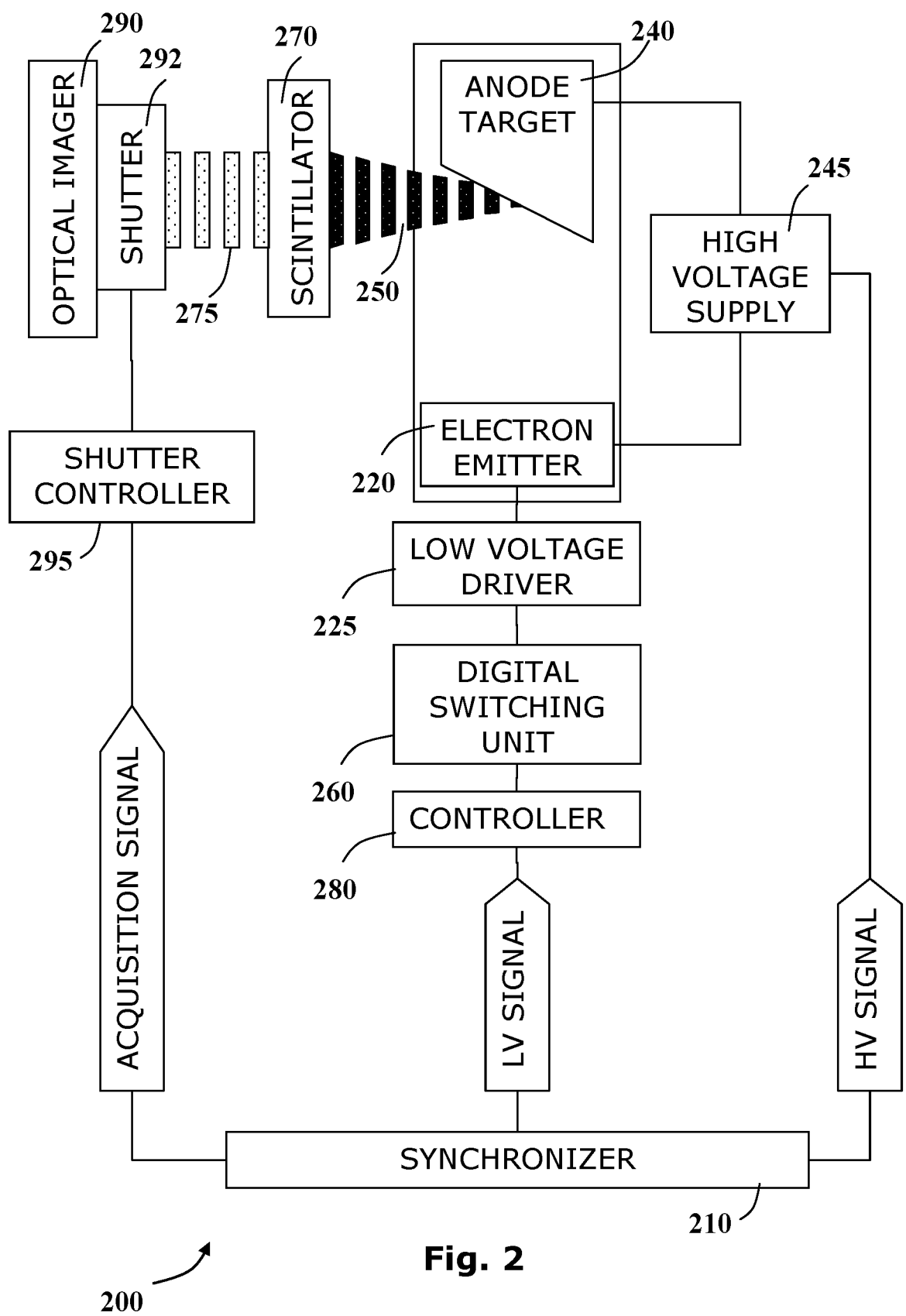
FIG. 2 is a block diagrams representing other embodiments of a switchable X-ray source incorporating a synchronized optical imager.

With reference to the block diagram of FIG. 2 which represents another embodiment of a switchable x-ray source 200 incorporating an synchronized optical imager 290.

The x-rays 250 emitted by the x-ray source 240 may be directed towards a scintillator 270 such that the scintillator 270 fluoresces when a pulse of x-rays 250 is incident thereupon. The optical imager 290 is configured and operable to detect florescence 275 from the scintillator 270 when its shutter 292 is open.

A shutter controller 295 is provided to trigger the shutter 292 of the optical imager when a shutter pulse is received.

It is noted that a synchronizer 210 may be provided to synchronize a shutter signal with the electron emission activation signal to further control the imaging duration of the system. Accordingly, the synchronizer may be operable to coordinate a high voltage (HV) signal, a low voltage (LV) signal and an acquisition signal.

The high voltage signal may be a function over time determining the characteristics of the high voltage amplitude of the electron accelerating potential produced by the high voltage supply 245. The signal profile of the HV signal may be controlled by the synchronizer 210 and coordinated with the LV signal and the acquisition signal to control the imaging rate of an x-ray device 200.

The low voltage signal may be a function over time determining the characteristics of the switching rate determined by the controller 280 of the digital switching unit 260. The digital switching unit 360 accordingly may activate the low voltage driver 225 for producing the low voltage activation potential provided to the electron emitting construct 220. The LV signal profile may be controlled by the synchronizer 210 and coordinated with the HV signal and the acquisition signal to control the imaging rate of an x-ray device.

The acquisition signal may be a function over time determining the sampling rate of the optical imager 290. Accordingly, by controlling the acquisition signal and coordinating it with the HV signal and the LV signal the synchronizer 310 may control the imaging rate of an x-ray device 200.

Figure 3:
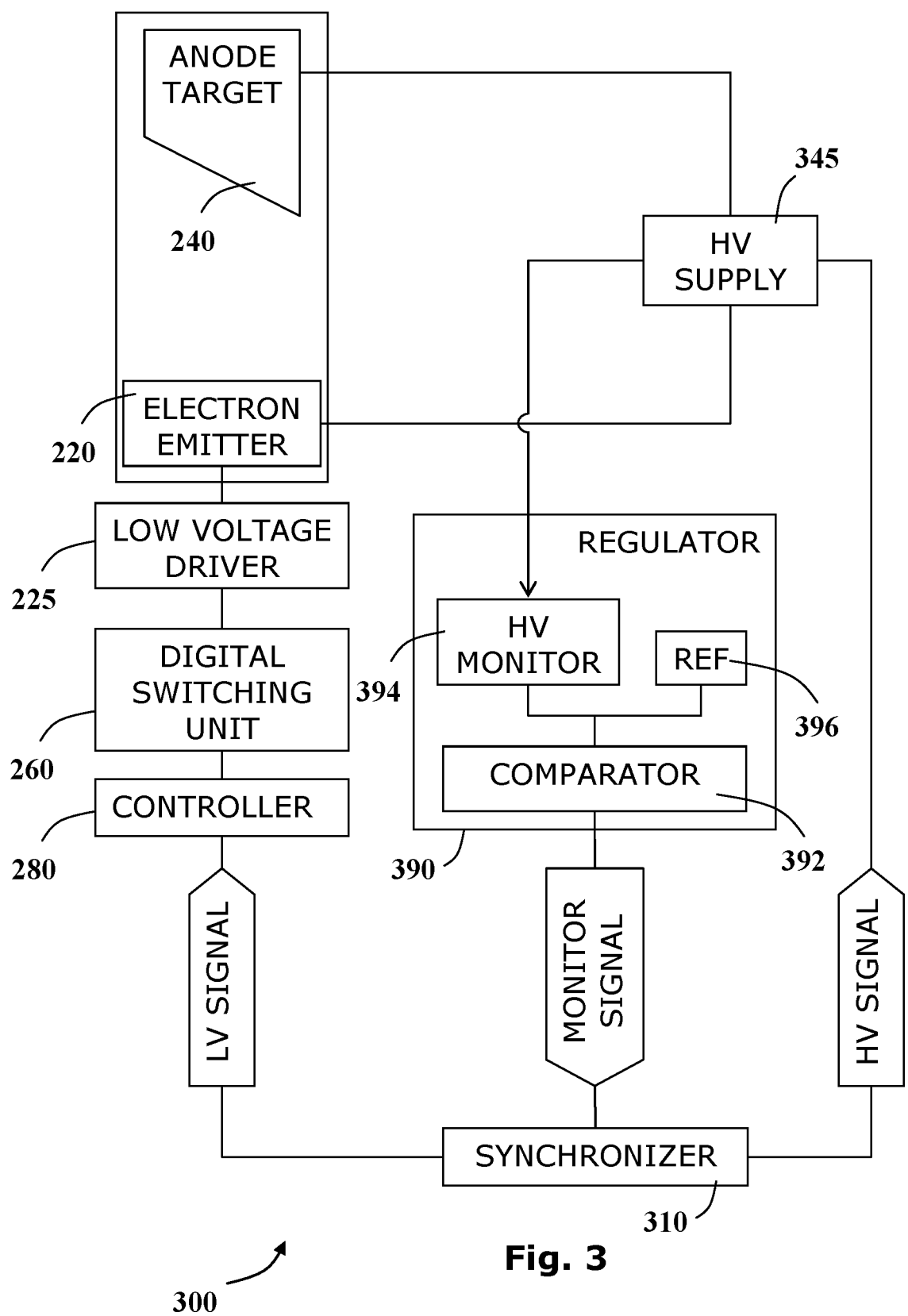
FIG. 3 is a block diagram representing how a regulator may be integrated into embodiments of the switchable X-ray sources.

With reference now to the block diagram of FIG. 3, representing how a regulator 390 may be integrated into embodiments of the switchable X-ray sources 300. The regulator includes a High Voltage Supply monitor 394 and a comparator 392.

The regulator 390 is in communication with the synchronizer 310 and operable to send a monitor signal thereto indicating if the Low Voltage signal should be activated.

The High Voltage Supply monitor 394 is configured and operable to monitor the high voltage supply 345 for example by measuring potential difference between the electron emitter 320 and the anode target 340.

The comparator 392 is configured and operable to compare the monitored value of High Voltage Supply with at least one Reference value stored in a memory unit 396 and to generate a monitor signal. Optionally the monitor signal may be an analog signal indicating the difference between the monitored value of the HV supply and the reference value. Alternatively, the monitor signal may be a digital signal perhaps a single bit taking a value of ONE if the low voltage driver should be activated and a value of ZERO if the low voltage driver should not be activated.

Figure 4A:
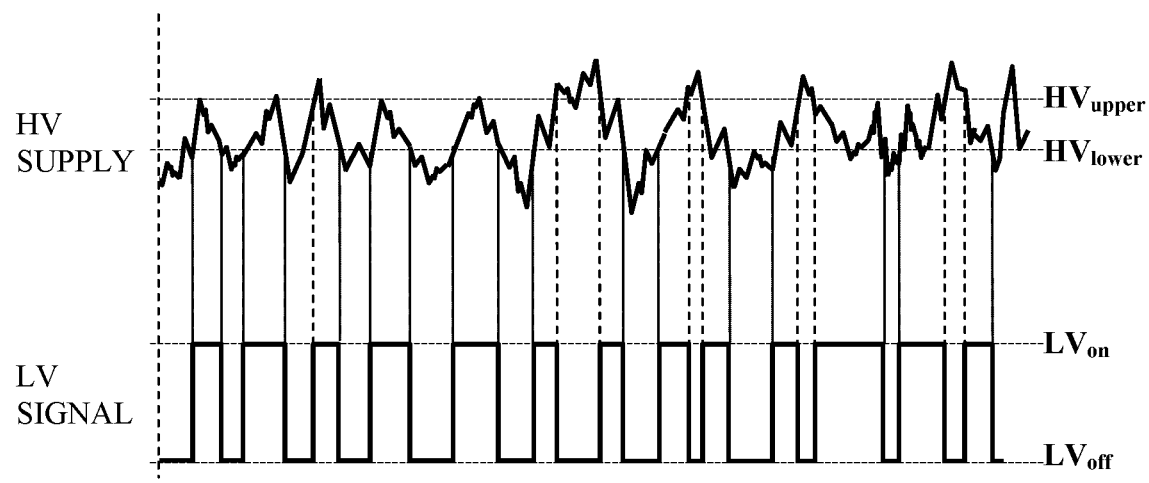
FIGS. 4A and 4B are graphic representations indicating how a low voltage signal may be synchronized with variable high voltage supply to maintain an X-ray power within a required range.

For example, with reference to FIG. 4A, the Low Voltage signal may triggered to take a value of $LV_{on}$ whenever the monitored value of the high voltage supply lies between a first upper High Voltage threshold value $HV_{upper}$ and a lower High Voltage threshold value $HV_{lower}$. When the high voltage supply lies either above the first upper High Voltage threshold value $HV_{upper}$ or below the lower High Voltage threshold value $HV_{lower}$, the Low Voltage signal may triggered to take a value of $LV_{off}$.

Figure 5A:
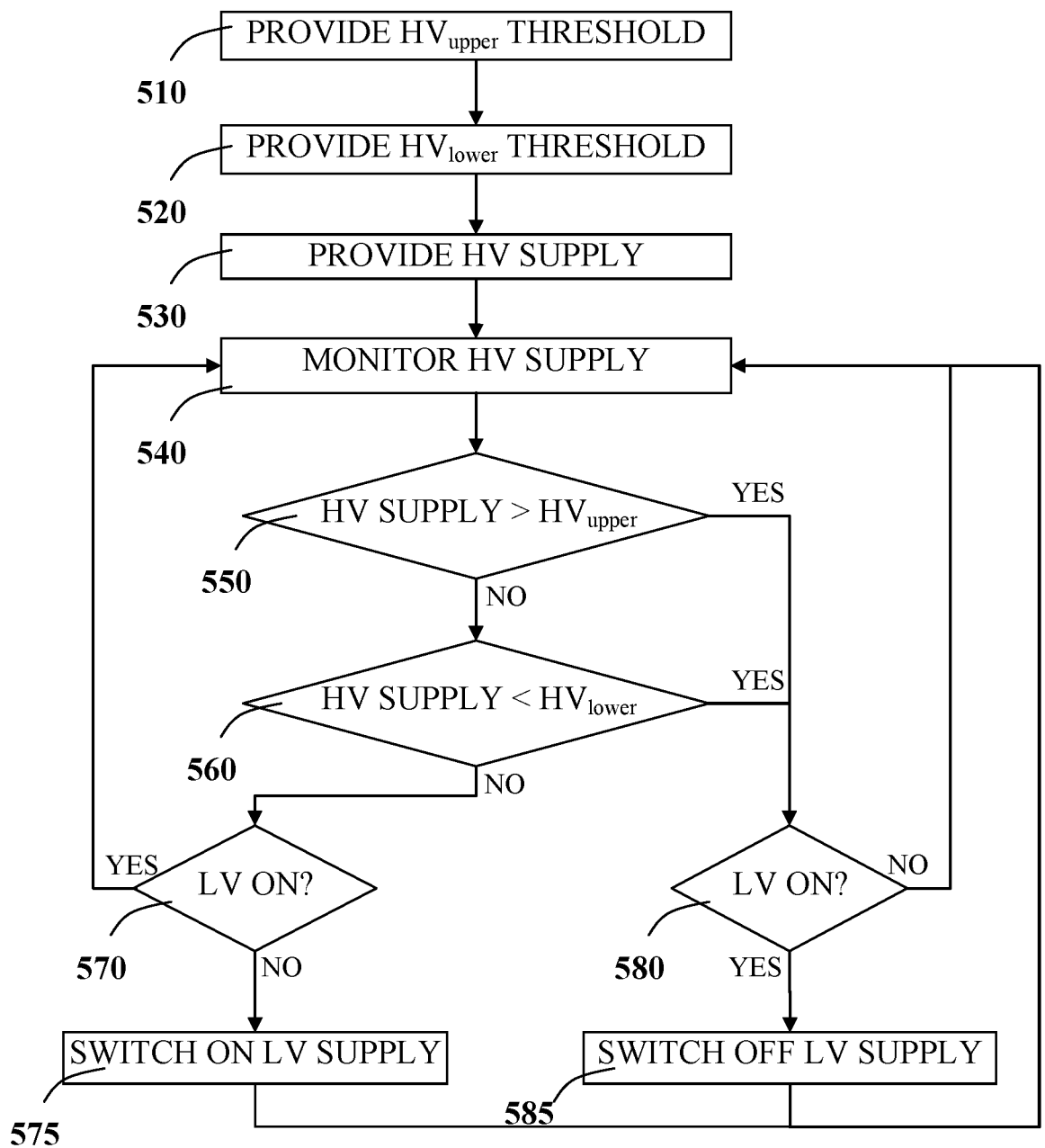
FIGS. 5A and 5B are flowcharts indicating how the low voltage signal may be controlled to regulate X-ray intensity.

The flowchart of FIG. 5A indicates a method by which the LV signal may be triggered by the comparator. The Upper High Voltage threshold value $HV_{upper}$, 510 and Lower High Voltage threshold value $HV_{lower}$ 520 are provided. The HV supply is then provided 530 between the emitter and the anode target. The HV supply is monitored 540. If the HV supply is above the Upper High Voltage threshold value $HV_{upper}$ 550 or below the Lower High Voltage threshold value $HV_{lower}$ 560 then, if the LV signal is active 580 then the LV signal is deactivated 585. Whereas if the HV supply is not above the Upper High Voltage threshold value $HV_{upper}$ 550 and not below the Lower High Voltage threshold value $HV_{lower}$ 560 then, if the LV signal is not active 570 then the LV signal is activated 575.

Figure 4B:
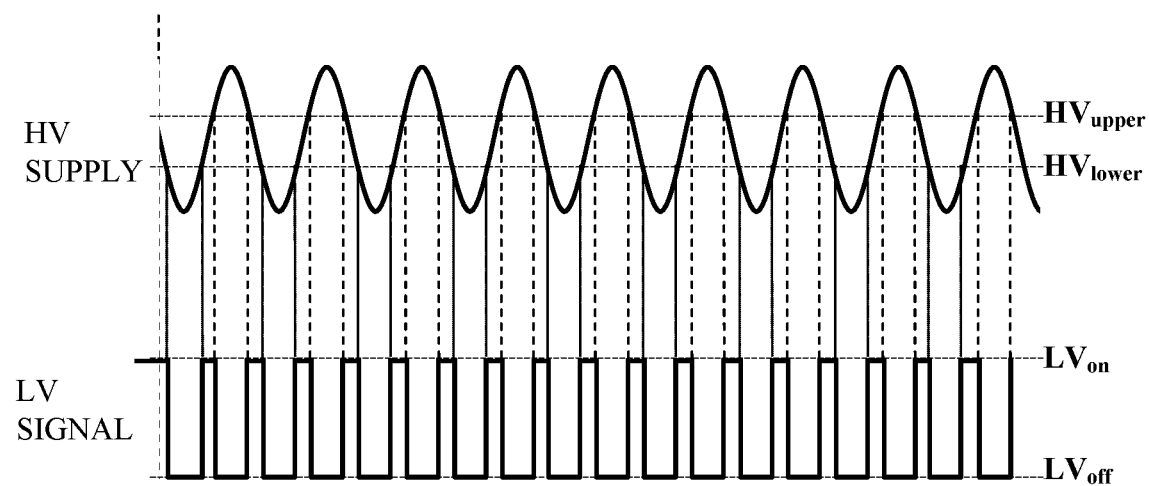

With reference to FIG. 4B, in alternative embodiments, a known HV Supply function HV(t) may be defined, for example a sinusoidal variation, a saw tooth or the like. If the HV Supply function HV(t) is known, then the low voltage signal may be time triggered.

Figure 5B:
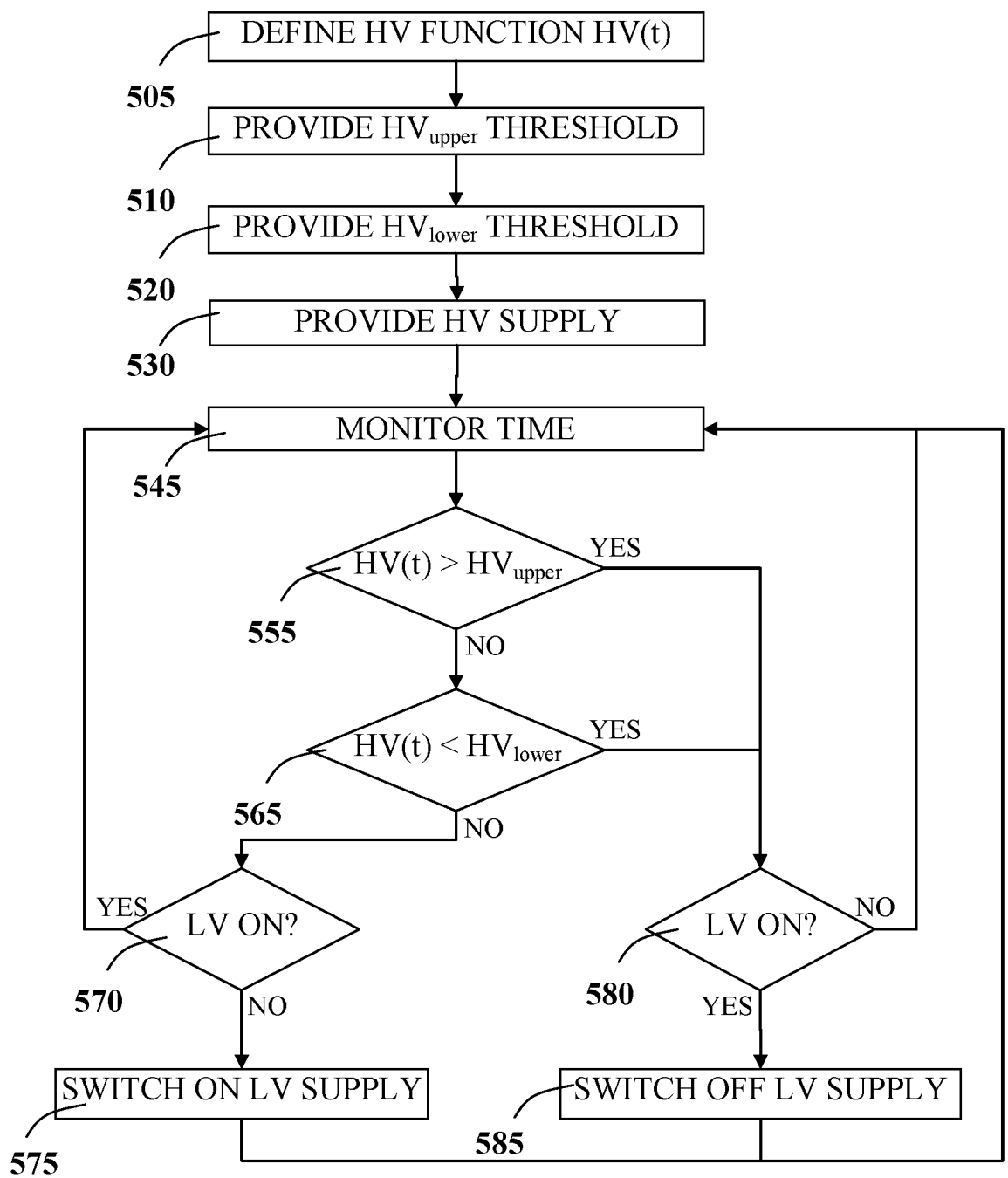

The flowchart of FIG. 5B indicates a method by which the LV signal may be triggered according to the time variable HV Supply function HV(t). The HV Supply function HV(t) is defined 505 and may be stored in a memory unit of the regulator. The Upper High Voltage threshold value $HV_{upper}$ 510, and Lower High Voltage Threshold value $HV_{lower}$ 520 are provided. The HV supply is then provided between the emitter and the anode target 530. Time is monitored 545 by a clock or other such time monitoring device of the regulator. Accordingly, a processor of the regulator may be operable to calculated the value of the HV Supply function HV(t) at each instant such that, if the value for HV(t) at a given time is higher than $HV_{upper}$ 555 or lower than $HV_{lower}$ 565, then when the LV signal is active, the LV signal is deactivated 585. Similarly, where the LV signal is not active then the LV signal may be activated 575 if the value for HV(t) is below the Upper High Voltage threshold value $HV_{upper}$ and above the Lower High Voltage Threshold value HViower.

Figure 6A:
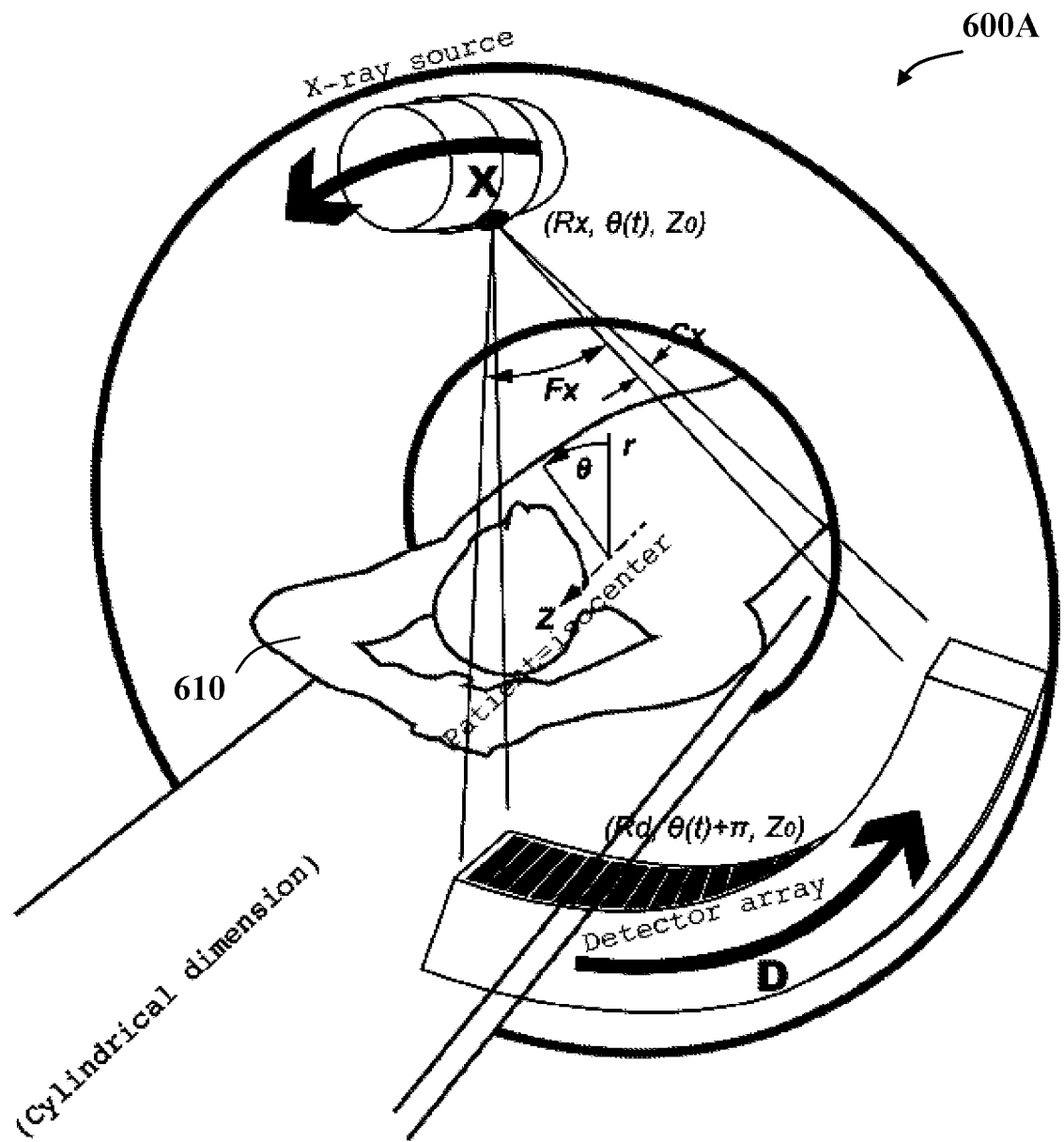
FIG. 6A is a schematic diagram of a computed tomography (CT) scanner to which a multi-dimensional X-ray analysis system may be incorporated.

Reference is now made to FIG. 6A which is a schematic diagram showing a computed tomography (CT) scanner 600A.

A CT scan, formerly known as a computerized axial tomography scan or CAT scan, produces a set of tomograpohoic X-ray images using X-ray measurements typically collected by rotating an X-ray source X and a detector D around a scanned object at diametrically opposed orientations. The detector D collects X-rays at various angles and these detections are combined using computer processing to produce cross-sectional images.

A set of such cross sectional images, or slices, may be combined to produce a three dimensional image of the subject.

A subject 610 may lay along the isocenter focus of the X-ray imager. It is noted that where the X-ray source X is positioned at polar coordinates (Rx, θ(t), Z0), a set of detectors D is arranged in an arc centered at (Rd, θ(t)+π, Z0), which is diameterically opposed to the X-ray source X and in the same plane. Accordingly, the detector D is configured to rotate to the same direction as the source X such that the diametric orientation is maintained.

The X-ray source X has a fan angle Fx measured within the X-Y plane and a cone angle Cx at right angles thereto. Where appropriate the detectors D has an angular extension of FX around the scanner and an angular extension along the Z axis of CX such that X-rays are collected over its entire extension.

Although FIG. 6A only shows the system set up at a single position $Z_0$, typically, the subject 610 is moved along the Z direction such that multiple slices may be imaged sequentially.

Figure 6B:
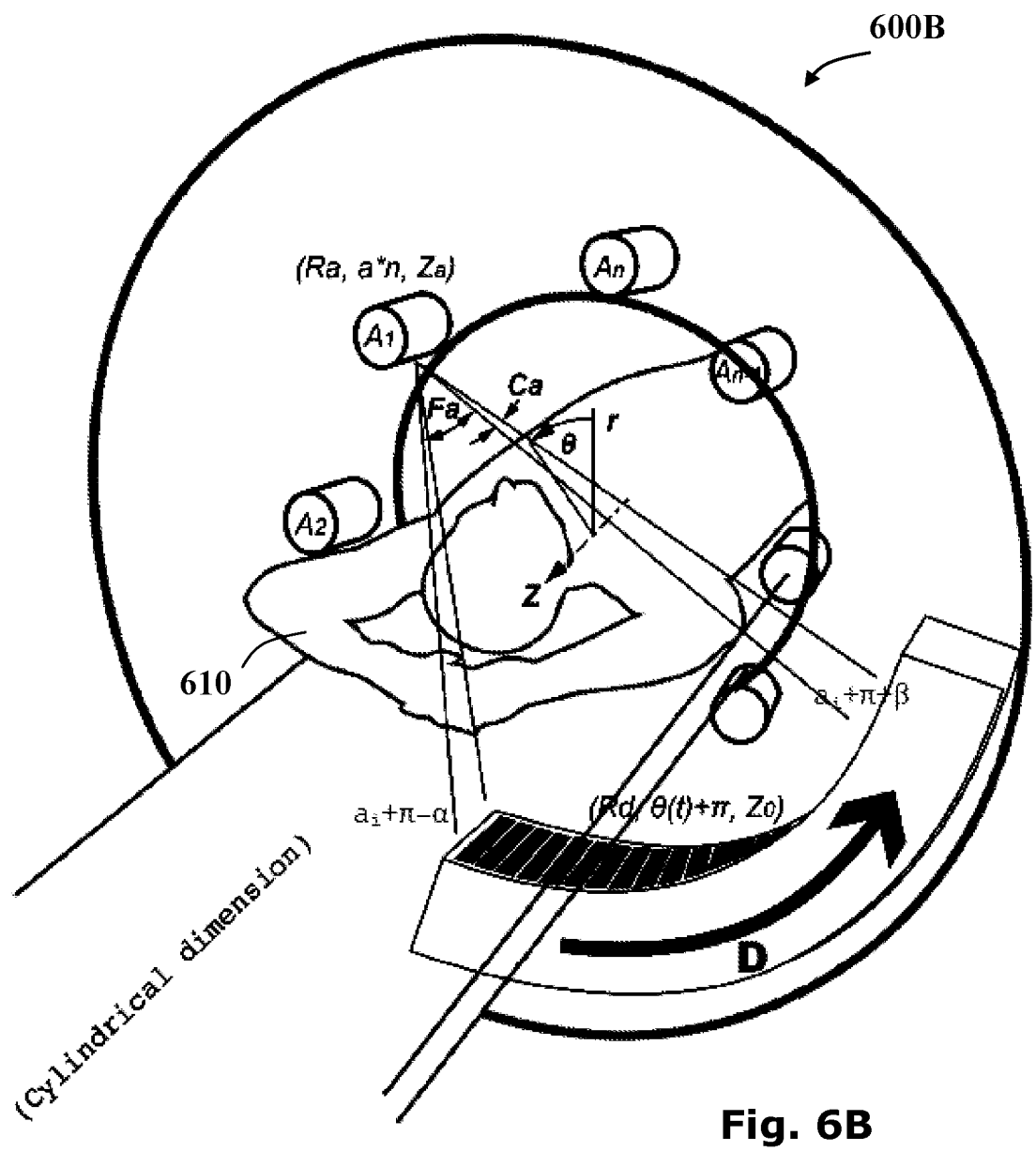
FIG. 6B is a schematic diagram of a computed tomography scanner incorporating a multi-dimensional X-ray analysis system.

Referring now to the schematic diagram of FIG. 6B, a multidimensional x-ray imager system 600B may be produced by incorporating an array of secondary x-ray sources A1-An into a computed tomography scanner. It is particularly noted that, where appropriate, such secondary sources A1-An may be retrofitted to existing CT scanners as required to produce multidimensional analysis.

According to the example, an array of n secondary x-ray sources A1-An are arranged, possibly at equidistant intervals, around the central axis such that each secondary source has coordinates of (Ra, ai, Za).

Additionally or alternatively, it is noted that the where required, the secondary sources A1-An may be in an irregular array at uneven angles.

Typically, the individual x-ray sources A1 to An are individually controlled and may be operable to generate different energy levels independently from each other. Furthermore the individual x-ray sources A1 to An are not necessarily identical and may have different energy ranges from each other and from X.

It is particularly noted that each secondary source A1 to An has a fan angle Fa and cone angle Ca which may be selected so as to cover the whole face of the set of detectors D when they are orientated at a diametrically opposed angle with their center at (Rd, ai+π, Z0).

Additionally or alternatively, each secondary source Ai projects X-rays having a characteristic energy level Ei towards D only when D's circumferential position θ(t)+π is in the range of ai+π−α to ai+π+β.

It is particularly noted that because the X-rays collected from the secondary sources A1 to An are in different energy ranges to those collected from the primary source X, multi-spectral information may be generated.

It is a particular feature of the embodiment that it is not necessary to install a second rotating x-ray source or switching the primary x-ray source X between different energy levels. Furthermore, it is unnecessary to install secondary detectors.

Figure 7A:
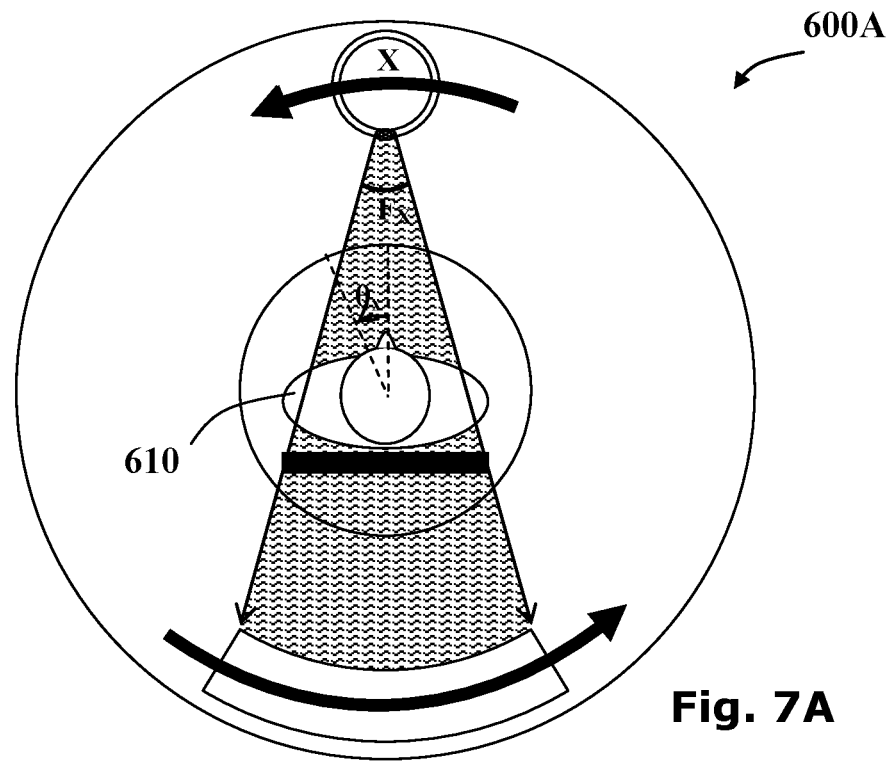
FIGS. 7A and 7B are schematic cross sections of a CT scanner indicating the configurations of an X-ray source and detector.
Figure 7B:
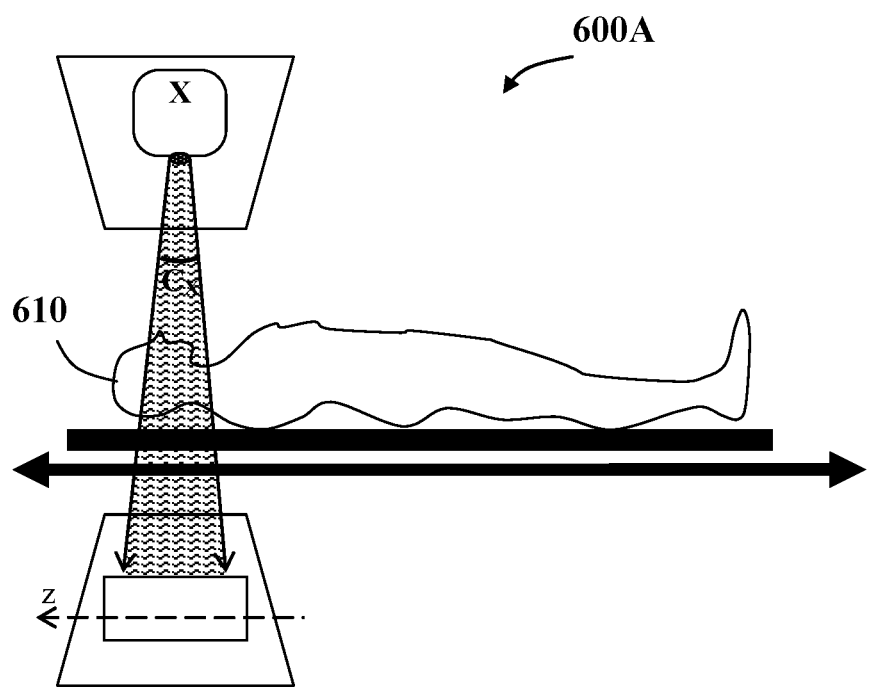

Referring now to the schematic cross sections FIGS. 7A and 7B, a CT scanner 600A including a rotating x-ray source and an opposing rotating detector is indicated. FIG. 7A shows the cross section in the X-Y plane whereas FIG. 7B shows the cross section in the Y-Z plane.

It is noted that the subject 610 may be exposed to X-rays from the primary source X continually as the primary source rotates about the central axis.

Figure 8A:
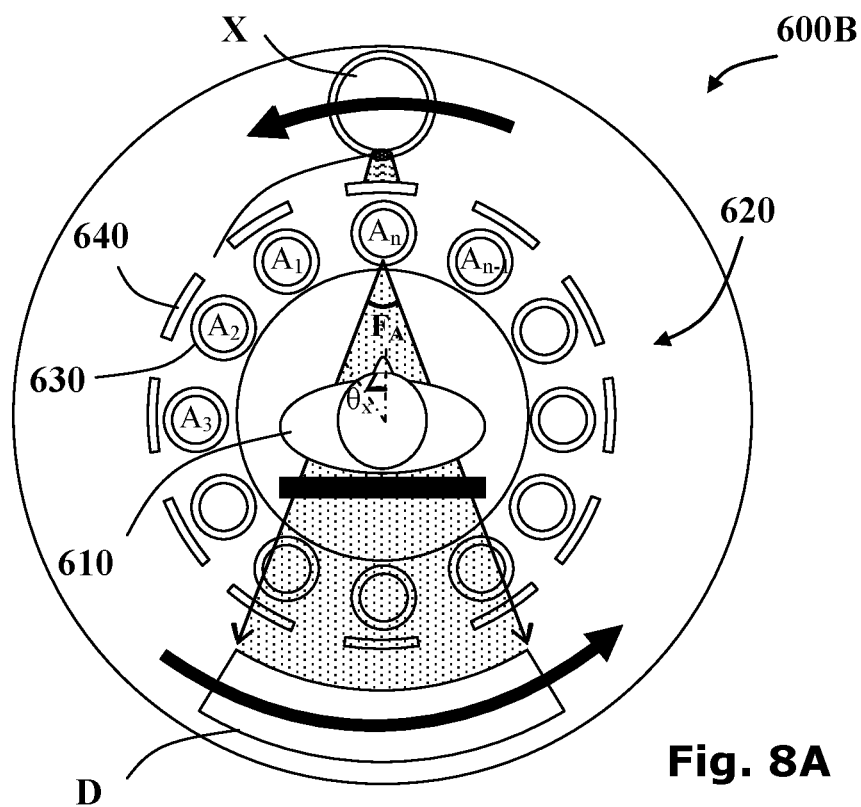
FIGS. 8A and 8B are schematic cross sections of a possible configuration of a CT scanner incorporating an array of static X-ray sources of a multi-dimensional X-ray analysis system.
Figure 8B:
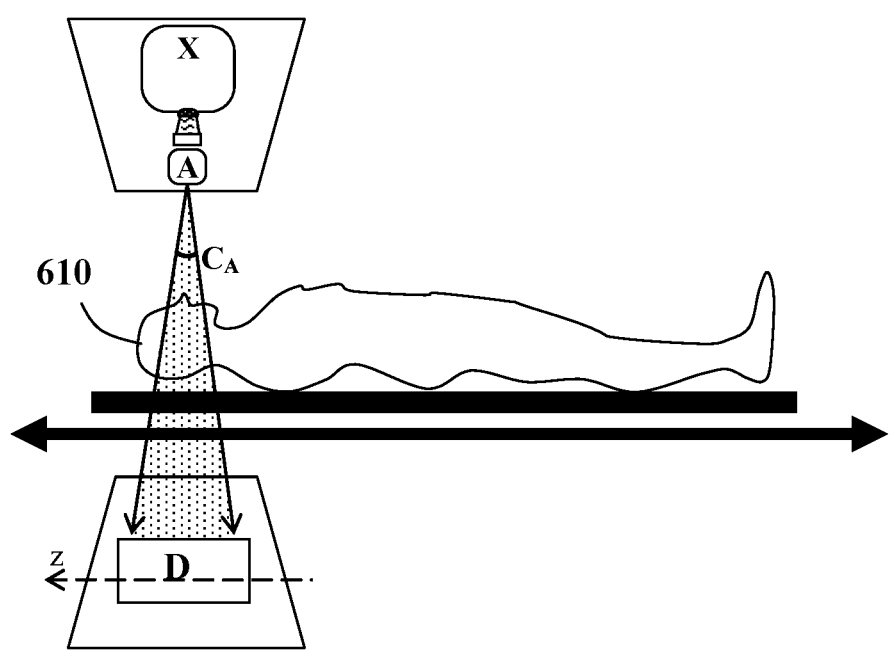

With reference now to the schematic cross sections FIGS. 8A and 8B, the CT scanner 600B may be enhanced by the addition of the multi-dimensional X-ray analysis system 620. FIG. 8A shows the cross section in the X-Y plane whereas FIG. 8B shows the cross section in the Y-Z plane.

An array of static secondary X-ray sources A1-An are arranged around an inner circumference of the CT scanner. It is noted that each secondary x-ray source 630 may have an associated x-ray shield 640 configured to prevent x-rays from the primary source X from reaching the subject 610 and the detector D at the same time as x-rays from the secondary source.

Figure 9A:
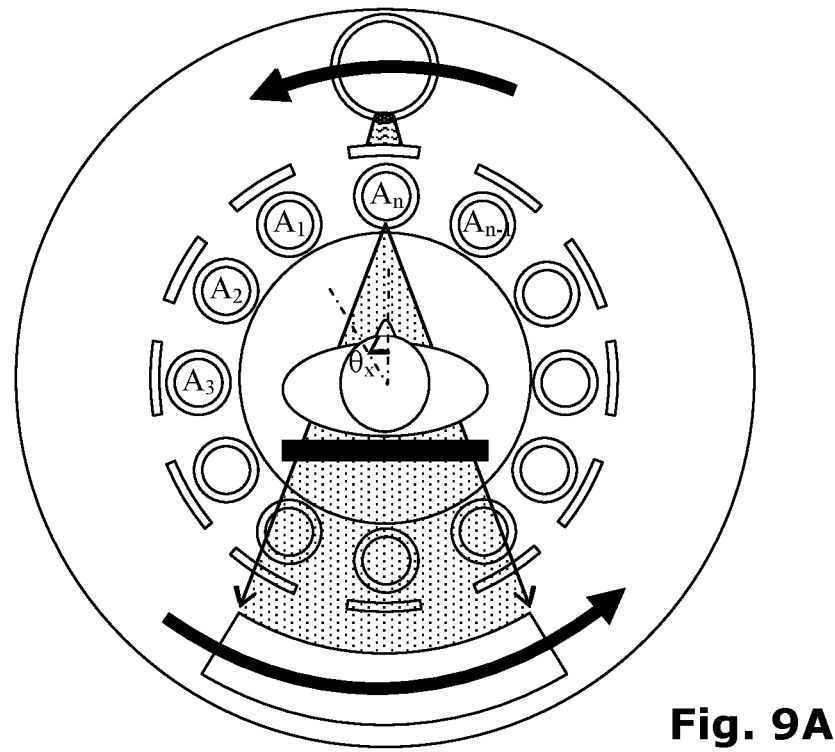
FIGS. 9A, 9B, and 9C are further schematic cross sections of a possible multi-dimensional X-ray analysis system incorporated into a CT scanner indicating how the X-ray detector is exposed to X-rays from various sources at various angles as the detector rotates about the central axis.
Figure 9B:
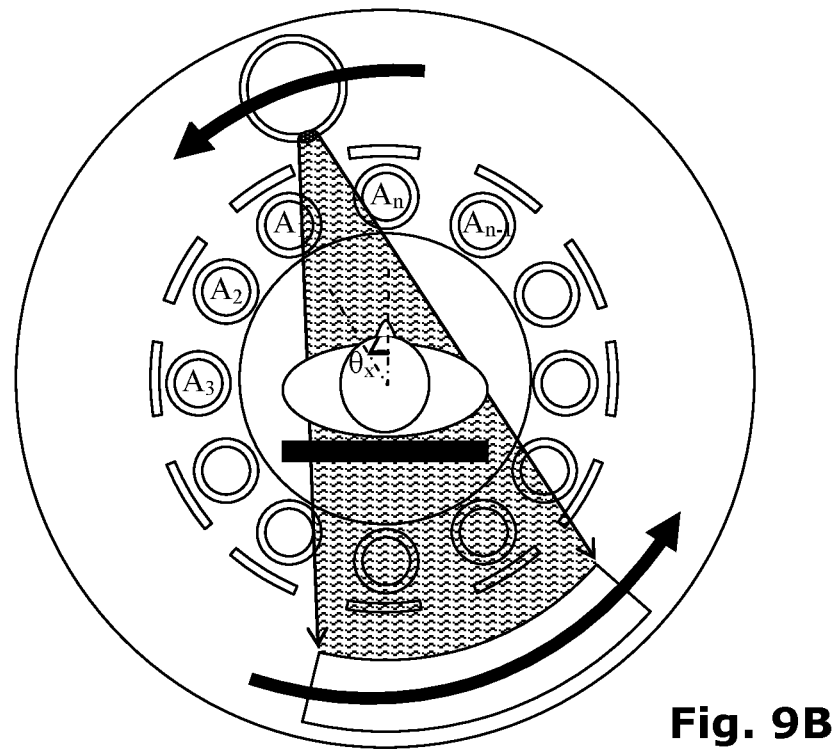
Figure 9C:
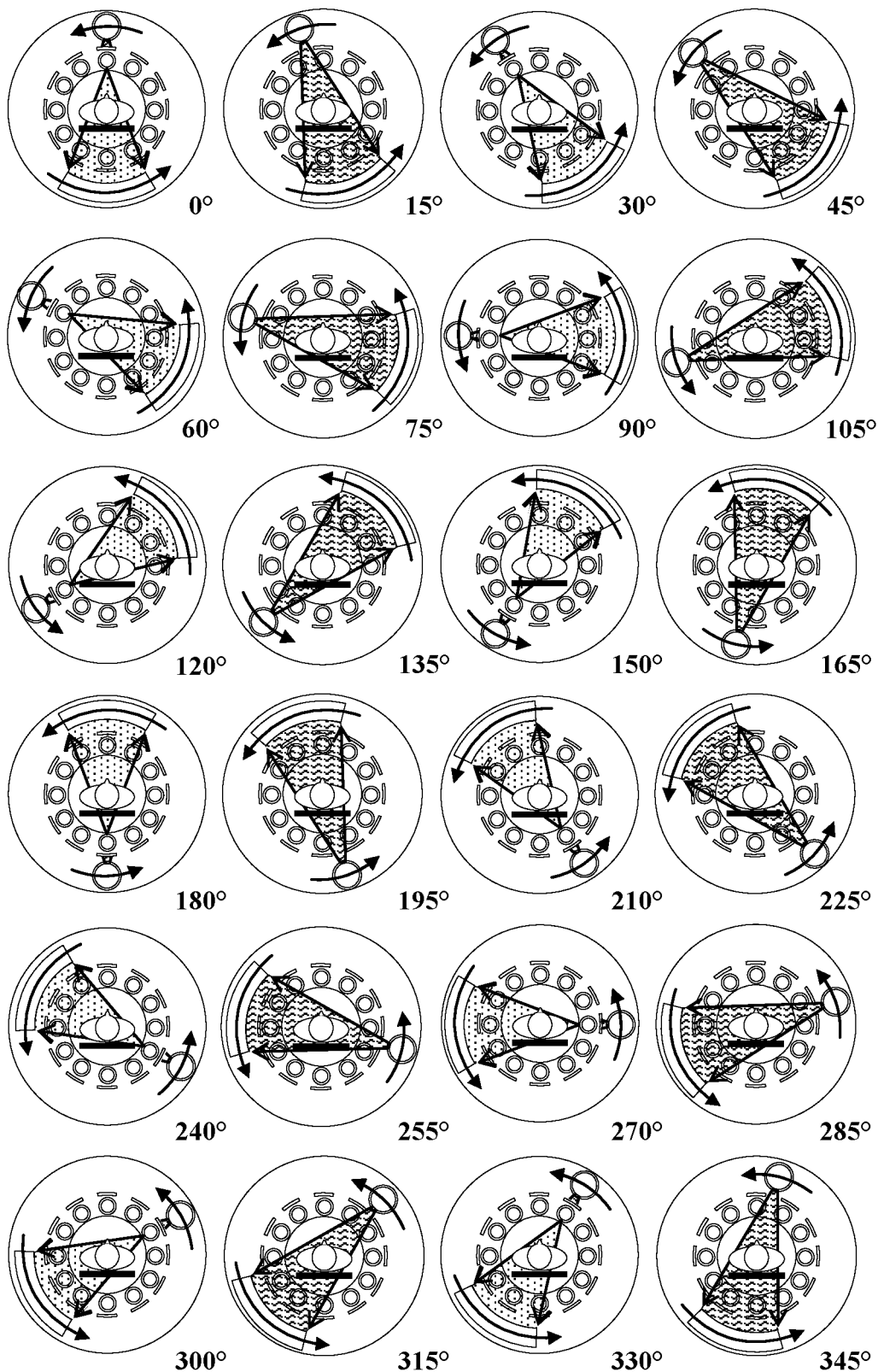

Accordingly, as illustrated in the schematic cross sections of FIGS. 9A, 9B, and 9C, the source from which x-rays are detected by the detector is dependent upon the angle of the detector and primary x-ray source.

In FIG. 9A the angle θ(x) of the primary x-ray source is the same as the angle an of a secondary x-ray source Accordingly, the shield associated with secondary source An blocks x-rays from the primary source X and only x-rays from the secondary source An reach the detector. It is further noted that the subject is only exposed to x-rays from the secondary source during this period and therefore x-ray exposure may be significantly reduced.

FIG. 9B shows the system at the instant when the angle θ(x) of the primary x-ray source lies between the angle an of the nth secondary source An and the angle a1 of the first secondary source A1. Here the x-rays from the primary source are not blocked and therefore reach the detector via the subject.

For completeness, FIG. 9C illustrates the system at various angles of the rotation of the primary source x-ray about the axis. The secondary sources are only activated when the detector is diametrically opposed thereto, thus:

the first secondary detector A1 is only activated for a short duration δtA while the primary detector X reaches a rotation angle of 30°;
the second secondary detector A2 is only activated for a short duration while the primary detector X reaches a rotation angle of 60°;
the third secondary detector A3 is only activated for a short duration while the primary detector X reaches a rotation angle of 90°;
the forth secondary detector A4 is only activated for a short duration while the primary detector X reaches a rotation angle of 120°;
the fifth secondary detector A5 is only activated for a short duration while the primary detector X reaches a rotation angle of 150°;
the sixth secondary detector A6 is only activated for a short duration while the primary detector X reaches a rotation angle of 180°;
the seventh secondary detector A7 is only activated for a short duration while the primary detector X reaches a rotation angle of 210°;
the eighth secondary detector A8 is only activated for a short duration while the primary detector X reaches a rotation angle of 240°;
the ninth secondary detector A9 is only activated for a short duration while the primary detector X reaches a rotation angle of 270°;
the tenth secondary detector A10 is only activated for a short duration while the primary detector X reaches a rotation angle of 300°;
the eleventh secondary detector A11 is only activated for a short duration while the primary detector X reaches a rotation angle of 330°; and
the twelfth secondary detector A12 is only activated for a short duration while the primary detector X reaches a rotation angle of 0°.

Figure 9D:
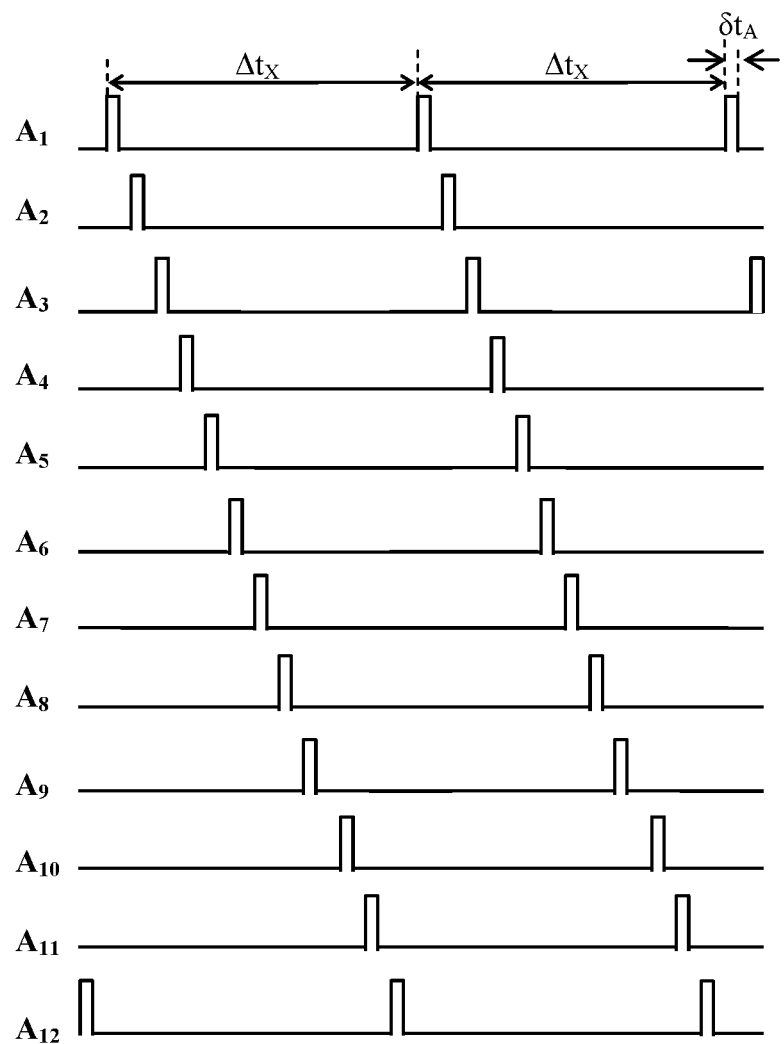
FIG. 9D indicates the activation signals profiles for each of X-ray source in an example of an array having twelve static X-ray sources arranged around the central axis.

FIG. 9D indicates the corresponding activation signal profiles for each of X-ray source in an example of an array having twelve static X-ray sources arranged around the central axis. It is noted that the duration of each pulse is δtA which corresponds to the length of time during which the detectors circumferential position θ(t)+π is in the range of ai+π−α to ai+π+β (see FIG. 3B). The total time for the primary source to complete full rotation is given by Δtx.

It is further noted that because each secondary source is independently controlled, it is possible to provide a high degree of control the exposure of the subject to x-rays. Thus for example, the intensity of the x-rays required for each orientations may be kept to a minimum requirement.

By way of illustration, at certain z positions, the intensity of x-rays from the third and ninth secondary sources which are emitted at 90 degree and 270 degree angles may need to penetrate the boney pelvis in order to be detected and therefore may need to be of much higher intensity than, say the x-rays from the sixth or twelfth secondary sources. In this manner the subject's exposure to x-ray radiation may be carefully modulated and controlled to be at a minimum with no resulting loss of information.

Additionally or alternatively, the secondary x-ray sources may themselves be operable to rotate around the central axis if required.

Although only a circular system with 12 secondary detectors at regular 15 degree intervals is represented in FIGS. 9A-D, it will be appreciated that other systems may use more or fewer secondary detectors at various regular or irregular intervals as required. It is particularly noted that where appropriate the secondary detectors may be arranged in an arc of the circle rather than spaced around the complete perimeter of the circle as indicated in the figures for illustrative purposes only.

Figure 10B:
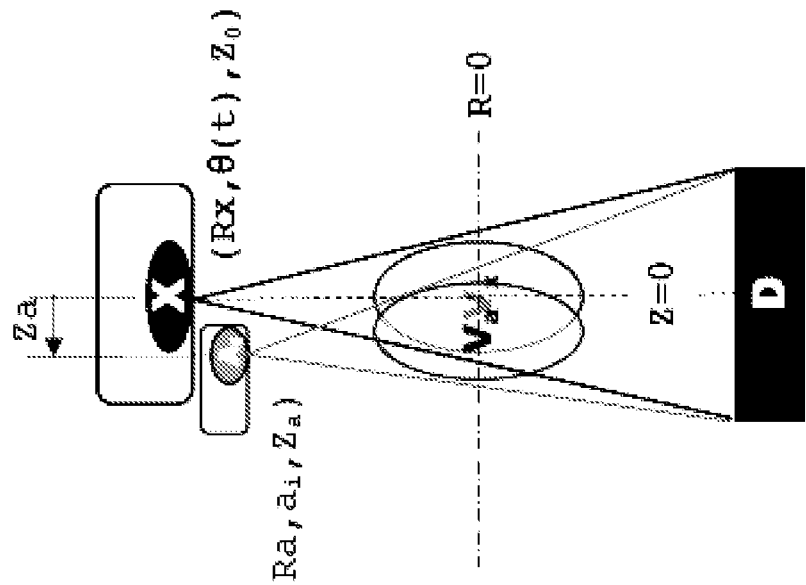
FIGS. 10A and 10B indicate possible dimensions for a primary CT X-ray source, a secondary source of the multi-dimensional and a common X-ray detector.
Figure 10A:
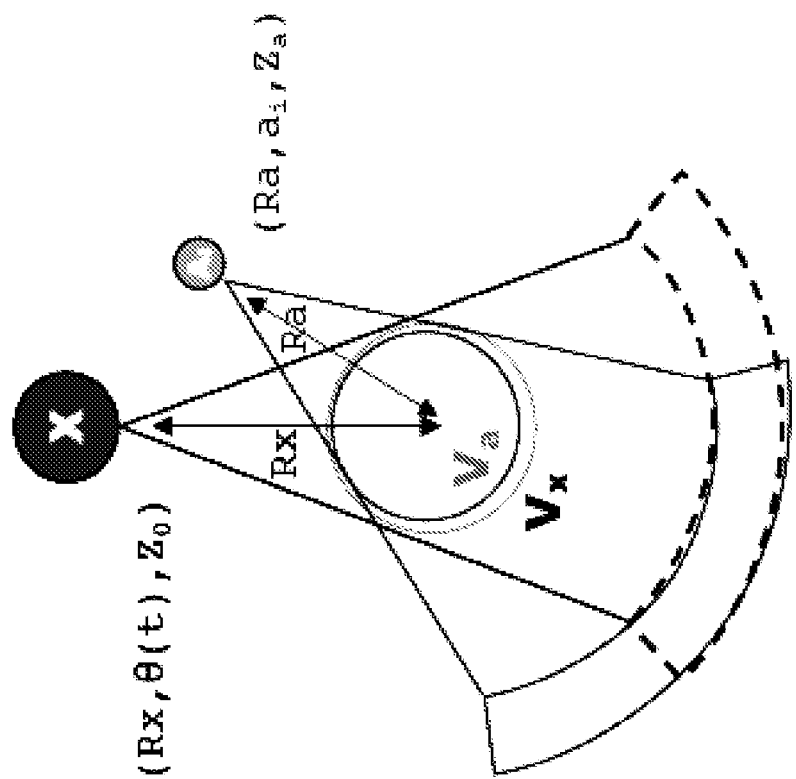

FIGS. 10A and 10B indicate possible dimensions for a primary CT X-ray source, a secondary source of the multi-dimensional and a common X-ray detector.

It is noted that in other embodiments, the z positions of the secondary sources A1-An are selected such that they do not shield the x-rays from the primary source X. Thus the position Za of the secondary sources my be offset by an amount δz.

In this case, at scan level=0 (Z0), The field of vision Va of the secondary sources A1-An is different from the field of vision Vx of the primary source X by the offset Za.

Where required the secondary sources A1-An may be installed at smaller radius Ra that the radius Rx of the primary source X such that they are closer to the patient and the projections from the secondary sources A1-An are not interfered by the primary source X.

Notably, each secondary source A1-An may have a larger fan angle FA than the fan angel FX of the primary source X (Fa>Fx). Even where A1-An cover the whole of the detector D, Va can be smaller than Vx.

Where required the rotation of the detector D may be controlled so as to separate the image collected from the primary source X from the images collected from the secondary source A1-An. In other embodiments it may be possible to distinguish the image from the primary source X from the images collected from the secondary source A1-An in other ways even if they are superimposed upon one another, for example by using different frequencies, wavelengths, polarities, intensities and the like.

In order to produce high resolution X-rays, it is desirable for beams of electrons to be directed towards a narrow point along the anode target. However such narrow focused spots generate much heat and typically cause significant wear to the anode itself.

Various methods for reducing ware upon the anode include using a moving anode target such that the striking point of the electron beam may fall upon changing locations on the anode. A switchable X-ray emitter may enable a different method for reducing wear on a static target anode.

Figure 11:
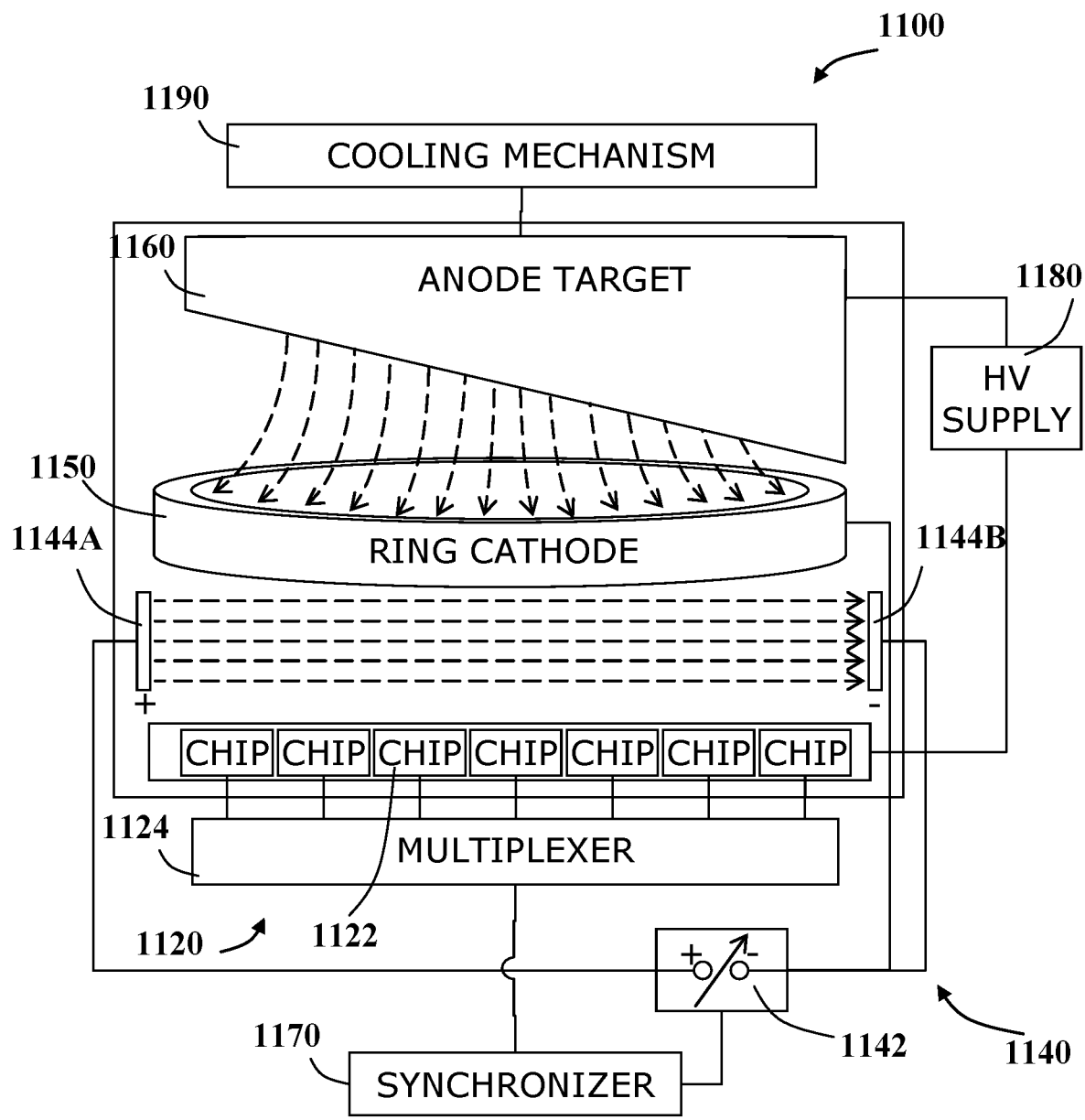
FIG. 11 schematically represents a switchable X-ray source incorporating multiple cathode chips and an electron beam directing mechanism.
Figure 12A:
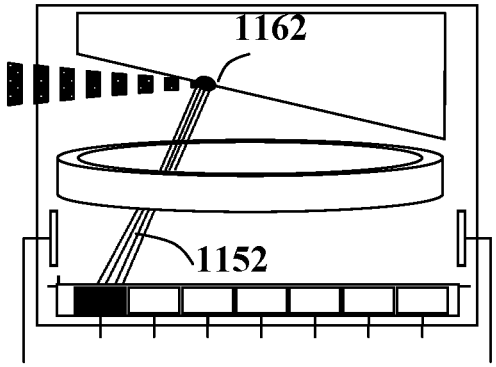
FIGS. 12A-F are a series of representations of the switchable X-ray source directing electron beams from multiple cathodes at a common point of the anode target.
Figure 12B:
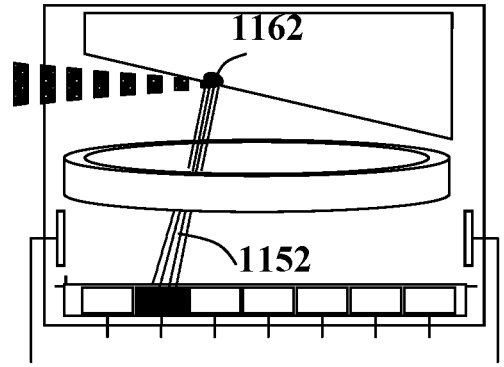
Figure 12C:
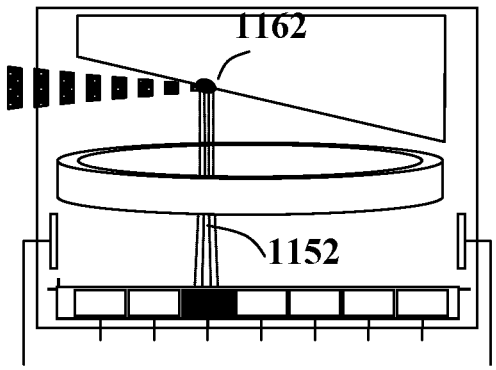
Figure 12D:
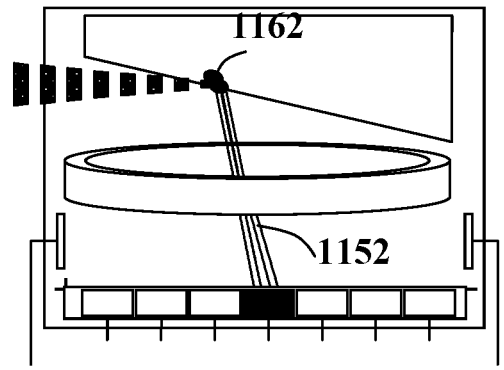
Figure 12E:
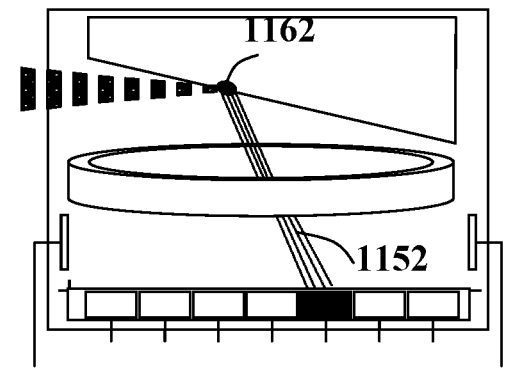
Figure 12F:
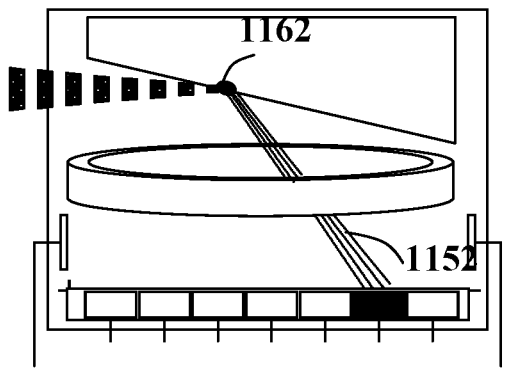
Figure 13A:
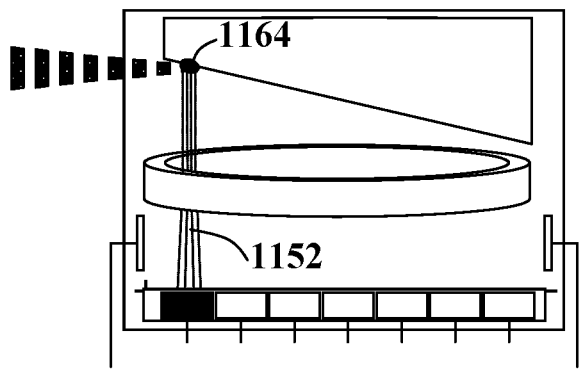
FIGS. 13A-F are a series of representations of the switchable X-ray source directing electron beams from multiple cathodes at different points of the anode target.
Figure 13B:
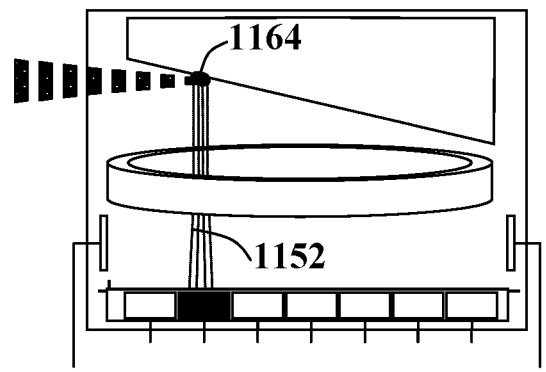
Figure 13C:
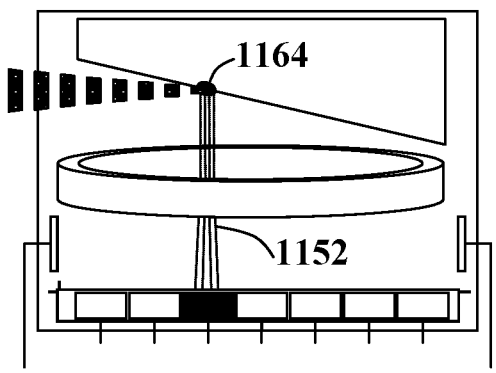
Figure 13D:
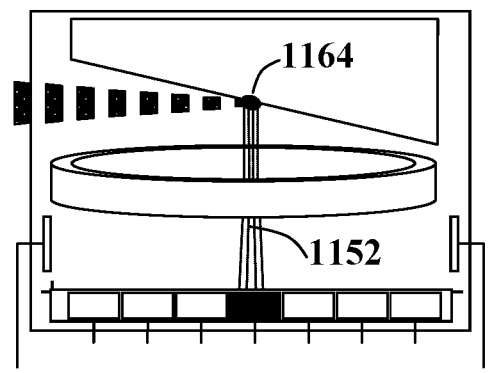
Figure 13E:
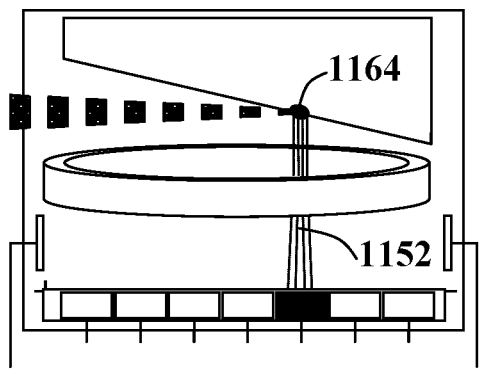
Figure 13F:
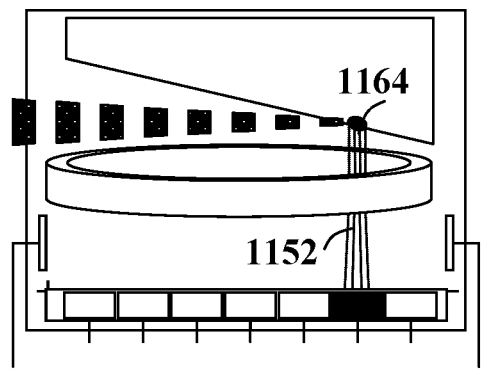

Reference is now made to FIG. 11 which schematically represents a switchable X-ray emitter device 1100 incorporating multiple cathode chips 1122 and an electron beam directing mechanism 1140.

The switchable X-ray emitter device 1100 includes a multi-chip cathode 1120, a static anode target 1160, a high voltage supply 1180, an electron beam directing mechanism 1140 and an electron beam shaping mechanism 1150.

The multi-chip cathode 1120 includes a switchable array of cold cathode electron sources 1122 each configured to emit electrons towards the electron anode target 1160, and a multiplexer switching system 1124 operable to switch between the electron sources 1122 of the array. Accordingly, the multiplexer 1124 may select the required cathode or cathodes to be activated at any given time.

The electron beam directing mechanism 1140 is operable to direct a stream of electrons towards a desired point upon the electron anode target. As required, as shown in FIGS. 12A-F, the electron beam 1152 produced by each cathode source 1122 may be directed towards a common spot 1162 on the anode target 1160.

Additionally, or alternatively, where preferred the electron beam directing mechanism may direct the beams from multiple cathode sources towards a different spot along the anode target as illustrated in FIGS. 13A-F. Accordingly, the striking point of the electron beam may be shifted across a static anode target to avoid wear at one particular point without needing to move the anode target itself.

According to some embodiments, the electron beam directing mechanism 1140 may include a variable DC power supply 1142 operable to maintain an adjustable potential difference between a pair of electrodes 1144A, 1144B. Thus an electric field is generated between the electrodes through which the electron beams emitted by the cathode sources 1122 pass before striking the anode target 1160. Electrons passing through the electric field are deflected accordingly. By selecting the potential difference the strength of the electric field may be adjusted so as to direct the electron beams to their required striking point. Other electron beam directing mechanisms will occur to those skilled in the art.

The electron beam shaping mechanism 1150 is provided to form the electron beam to a required shape, typically for reducing the diameter of the electron beam emitted by the cold cathode electron source. For example, a ring cathode may generate an inward force upon the negative electrons within the beam thereby reducing the cross section of an electron beam emitted by the cold cathode and passing therethrough before striking the anode target 1160.

A synchronizer or controller 1170 may be provided to coordinate the timings of the switching device, the electron beam directing mechanism 1140 and the electron beam shaping mechanism 1150. In particular, the potential difference generated by the electron beam directing mechanism 1140 is typically adjusted depending upon which cathode source 1122 is selected.

Figure 14:
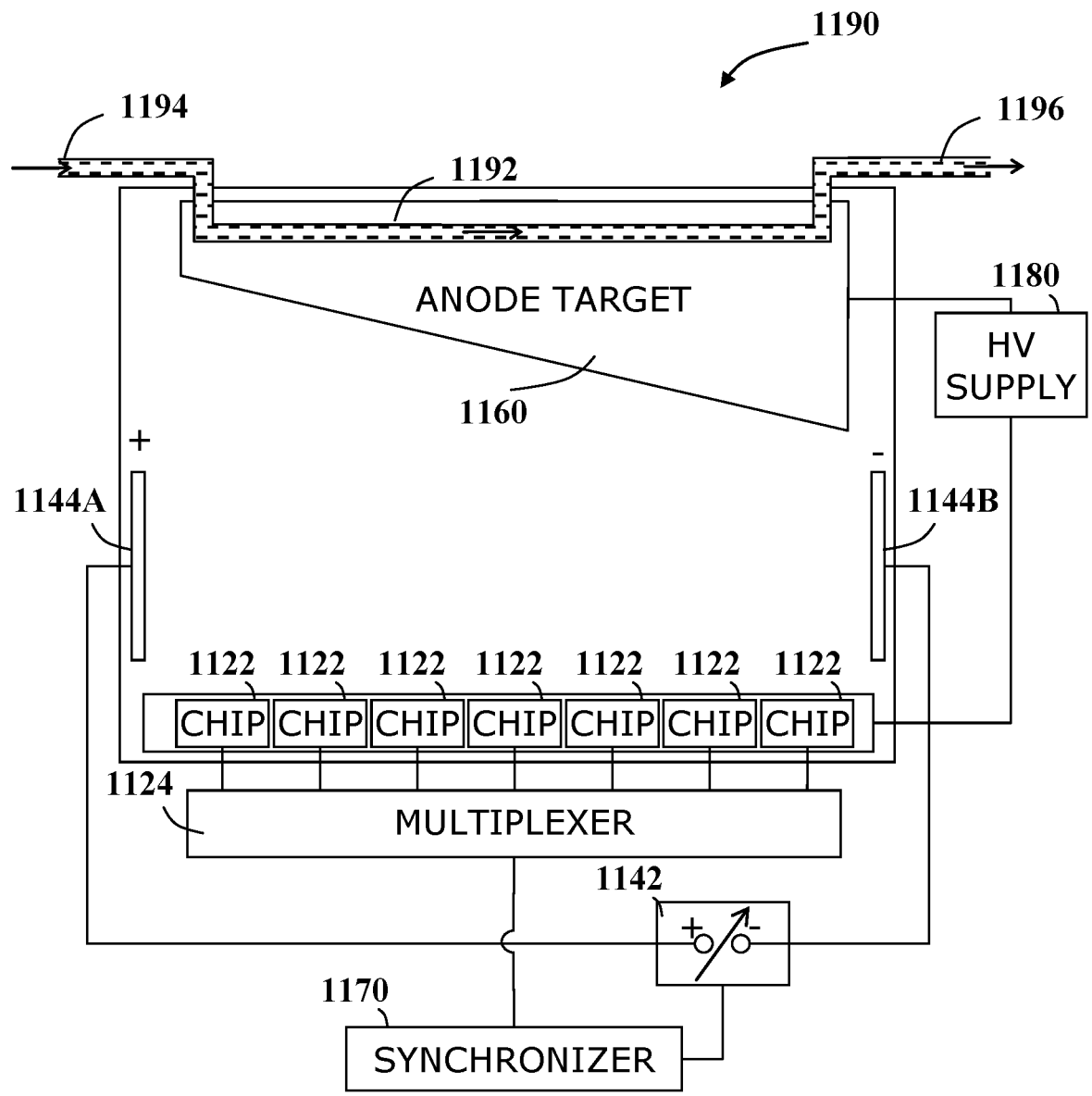
FIG. 14 schematically represents a possible anode cooling mechanism for a switchable X-ray source.

It is particularly noted that, an anode cooling mechanism 1190 may be provided to cool the anode target 1160 during use. Where the anode target is static, a fluid cooling mechanism 1192 may be incorporated therewithin. As schematically represented in FIG. 14 schematically represents a possible anode cooling mechanism for a switchable X-ray source may include one or more thermally conducting cooling pipe 1192 through which coolant passes from an inlet 1194 to an outlet 1196. The coolant, such as water, may carry heat generated by the anode away from the system.

It will be appreciated that the x-ray emitter device may be used in a method for generating a narrow beam of x-rays from an anode target. Such a method may include providing x-ray emitter device, comprising an array of cold cathode electron sources configured to emit electrons towards an electron anode target; providing a switching system for switching between the cold cathodes of the array; providing at least one electron beam directing mechanism; the switching system activating a first cold cathode to emit a stream of electrons; the electron beam directing mechanism directing the stream of electrons towards a first desired point upon the anode target; the switching system deactivating the first cold cathode to emit a stream of electrons; the switching system activating a next cold cathode to emit a next stream of electrons; the electron beam directing mechanism directing the stream of electrons towards a next desired point upon the anode target; the switching system deactivating the next cold cathode to emit a stream of electrons.

These steps of activating, directing and deactivating for each cold cathode may be repeated such that each cold cathode produces an electron beam incident upon different points of the anode target.

Technical Notes

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The scope of the disclosed subject matter is defined by the appended claims and includes both combinations and sub combinations of the various features described hereinabove as well as variations and modifications thereof, which would occur to persons skilled in the art upon reading the foregoing description.

The invention claimed is:

1. An x-ray emission system, comprising:
   an electron anode target;
   an array of cold cathode electron sources configured to emit electrons towards said electron anode target; and
   a switching system for switching between the cold cathodes of the array;
   wherein the x-ray emitter device further comprises:
   at least one electron beam directing mechanism operable to direct a stream of electrons emitted by the at least one cold cathode electron source towards a desired point upon the electron anode target, wherein said electron beam shaping mechanism comprises a ring cathode configured such that an electron beam emitted by the cold cathode passes therethrough before striking the anode target; and
   at least one electron beam shaping mechanism for reducing the diameter of an electron beam emitted by the at least one cold cathode electron source wherein said directing mechanism comprises a variable DC power supply operable to maintain a required potential difference between a pair of electrodes thereby generating an electric field and deflecting electron beams emitted by the cold cathodes.

2. The system of claim 1 wherein said at least one switching device comprises a multiplexer operable to switch sequentially between the cold cathode electron sources.

3. The system of claim 1 further comprising a synchronizer operable to coordinate the timings between the switching device, the electron beam directing mechanism and the electron beam shaping mechanism.

4. The system of claim 1 further comprising an anode cooling mechanism.

5. The system claim 4 wherein the anode cooling mechanism comprises at least one thermally conducting cooling pipe through which coolant passes from an inlet to an outlet.

6. The x-ray emission system of claim 1 wherein:
   the array of cold cathode electron sources comprises a field emission type electron emitting construct; and
   the switching system comprises:
   a low voltage driving circuit for activating said electron emitting construct;
   a high voltage supply for establishing an electron accelerating potential between said electron emitting construct and said anode;
   a digital switching unit operable to selectively connect and disconnect said low voltage driving circuit;
   a synchronizer; and
   at least one regulator in communication with the synchronizer and operable to send a monitor signal thereto indicating if the low voltage signal should be activated.

7. The system of claim 6 wherein the at least one regulator comprises:

a high voltage supply monitor configured and operable to monitor potential difference between the anode target and the electron emitter;

a memory unit storing at least one reference value; and a comparator configured and operable to compare the potential difference between the anode target and the electron emitter with the at least one reference value.

8. The system of claim 7 wherein the memory unit stores an Upper High Voltage Threshold value $HV_{upper}$.

9. The system of claim 7 wherein the memory unit stores a Lower High Voltage Threshold value $HV_{lower}$.

10. The system of claim 9 wherein the at least one regulator comprises:

a memory unit storing a High Voltage Supply Function $HV(t)$;

a time monitoring device; and a processor configured and operable to trigger the monitor signal when the High Voltage Supply Function $HV(t)$ returns a value outside a required range.

11. The system of claim 10 wherein the required range is bounded by an Upper High Voltage Threshold value $HV_{upper}$, and a Lower High Voltage Threshold value $HV_{lower}$.

* * * * *